United States Patent [19]

Kametaka et al.

[11] 4,260,813
[45] Apr. 7, 1981

[54] PROCESS FOR THE CONTINUOUS PRODUCTION OF ETHYLENE GLYCOL MONOETHYL ETHER ACETATE

[75] Inventors: Norio Kametaka, Hiratsuka; Kuniomi Marumo, Fujisawa; Kiyonori Tokuda; Kazuo Sekiguchi, both of Shinnanyo, all of Japan

[73] Assignee: Showa Denko K.K., Tokyo, Japan

[21] Appl. No.: 8,341

[22] Filed: Jan. 31, 1979

[30] Foreign Application Priority Data

Feb. 2, 1978 [JP] Japan .................................. 53-9894
Feb. 2, 1978 [JP] Japan .................................. 53-9896

[51] Int. Cl.³ .................... C07C 67/03; C07C 67/54
[52] U.S. Cl. ............................ 560/234; 203/71; 203/73; 203/81; 203/DIG. 19; 568/877
[58] Field of Search ................ 560/234; 568/877; 203/81, DIG. 19, 71, 73

[56] References Cited

U.S. PATENT DOCUMENTS 2,862,962  12/1958  Ulvild et al. ...................... 560/234
3,700,726  10/1972  Johnson, Jr. et al. ............. 560/234

FOREIGN PATENT DOCUMENTS 43-16966  7/1968  Japan .................................. 560/234

OTHER PUBLICATIONS

Manufacturing Chemist, Nov. 1956, pp. 454–458.
Helfferich, Angew. Chem., 1954, 66, pp. 241–249.

*Primary Examiner*—Vivian Garner
*Attorney, Agent, or Firm*—Wenderoth, Lind & Ponack

[57] ABSTRACT

Ethyl acetate and an excess of ethylene glycol monoethyl ether are subjected to ester-interchange reaction at a temperature not exceeding 100° C. in the presence of a strongly acidic cation exchange resin as a catalyst. The resulting reaction mixture is distilled to recover the ethylene glycol monoethyl ether acetate formed. The unchanged reactants are recycled to the reaction zone for re-use, and the by-product ethanol is recovered in a highly pure form. This method can be continuously performed easily and effectively without the need to separate the catalyst or to employ complex distilling steps and without involving other difficulties.

9 Claims, 1 Drawing Figure

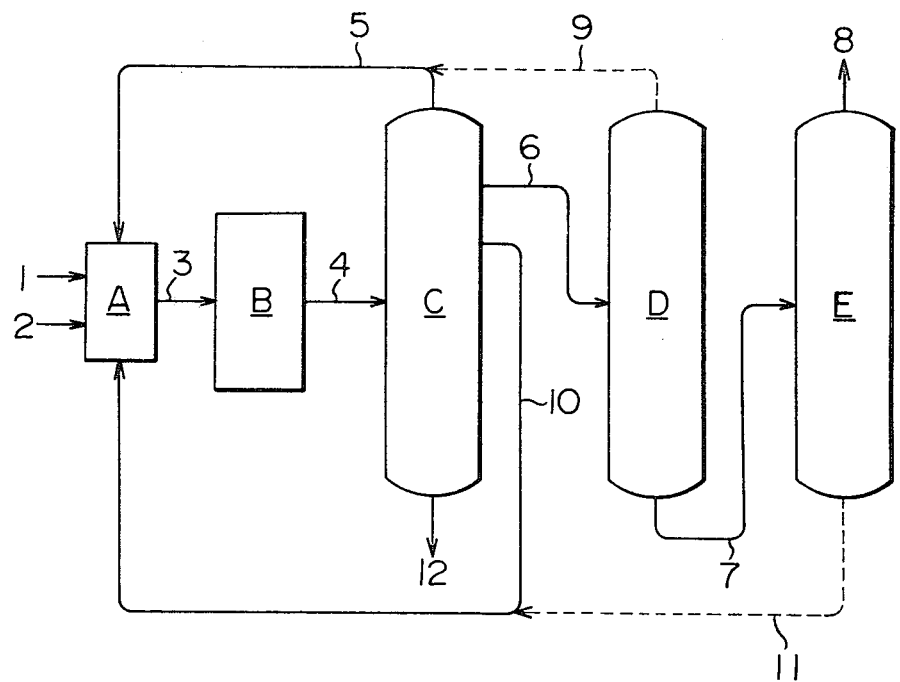

PROCESS FOR THE CONTINUOUS PRODUCTION OF ETHYLENE GLYCOL MONOETHYL ETHER ACETATE

This invention relates to an improved process for continuously producing ethylene glycol monoethyl ether acetate by an ester-interchange reaction or trans-esterification between ethyl acetate and ethylene glycol monoethyl ether.

Ethylene glycol monoethyl ether acetate is also called ethyl cellosolve acetate, and is well known as a solvent having superior properties. The term "cellosolve" is originally a trademark, but is used i this application as if it were a common noun because it is now widely accepted as such. This substance is extensively used as a solvent for the production of acrylic resin paints and also as a solvent for polyurethane resins, epoxy resins, nitrocellulose, etc.

Ethyl cellosolve acetate has been conventionally produced by esterifying ethylene glycol monoethyl ether, or ethyl cellosolve, with acetic acid in the presence of an acid catalyst, and this method is still in commercial use. The starting ethyl cellosolve is generally produced by an addition reaction between ethanol and ethylene oxide, and therefore, the exxpensive ethanol is consumed in a considerable quantity. Furthermore, since highly corrosive acetic acid is used in this esterification reaction, an anti-corrosive apparatus is disadvantageously required in commercial practice. Moreover, water is formed as a by-product in this esterification reaction, and since an azeotrope is formed between water and ethyl cellosolve and between water and ethyl cellosolve acetate, the distilling and separating operations for the reaction mixture are very complex. Another defect is that at the time of neutralizing the acid catalyst and unreacted acetic acid prior to the distillation of the ester, the desired ester, which has fairly high solubility in water, dissolves in water and is lost in the waste water.

Recently, methods were suggested for producing ethyl cellosolve acetate by an ester-interchange reaction between ethyl acetate and ethyl cellosolve in an attempt to eliminate the defects of the aforesaid esterification reaction. One of such methods is described in (1) Japanese Pat. No. 16966/1968, and another, in (2) U.S. Pat. No. 3,700,726.

This ester-interchange reaction is an equilibrium reaction expressed by the following equation (I). Ethanol formed as a by-product in this reaction forms an azeotrope (weight ratio at atmospheric pressure 31:69) with ethyl acetate present in the reaction system.

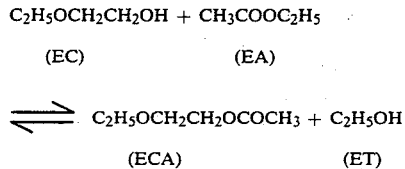

The above substances expressed by abbreviations have the following boiling points at atmospheric pressure.

| EC: ethyl cellosolve | 135.1° C. |
|---|---|
| EA: ethyl acetate | 77.1° C. |
| ECA: ethyl cellosolve acetate | 156.4° C. |
| ET: ethanol | 78.3° C. |
| EA/ET: ethyl acetate/ethanol azeotrope | 71.8° C. |

In the following description, the above abbreviations will often be used.

The starting EA can be commercially produced by the Tischchenko reaction of acetaldehyde and is available at low cost. EC, the other starting material, is produced by an addition reaction between ET and ethylene oxide as stated hereinabove. Since ET is formed as a by-product in the ester-interchange reaction of equation (I), the effective utilization of ET for the production of EC would obviate the consumption of ET as in the conventional esterification method described hereinabove. Since ethylene oxide is a very highly reactive substance, unless ET is of sufficiently high purity, impurities contained in ET will react with ethylene oxide to form by-products. Separation of these by-products is difficult, and the yield of the desired EC decreases. In practice, therefore, the EA/ET azeotrope cannot be used directly as an Et component for the production of EC.

The production of ECA by the ester-interchange reaction (I) essentially poses trouble some problems. For example, ET occurs as a by-product, and forms a minimum boiling point azeotrope with EA used as a reactant. Because separation of the azeotrope into EA and ET is not easy, these components are difficult to re-use. Moreover, Ea, ET and the EA/ET azeotrope which are involved in this reaction have boiling points close to one another. These problems make it difficult to produce ECA commercially in an economical way. The previously suggested, publications methods disclosed in (1) and (2) above meet with difficulty in separating or regenerating the catalyst, and this makes the process steps more complex. No entirely satisfactory method has thus been established for the commercial production of ECA.

Before disclosing the invention, we shall first briefly explain the methods (1) and (2) suggested heretofore.

The method (1) is a batch method which comprises subjecting EC, produced by the reaction of ethylene oxide with ET, and an excess of EA (about 3 moles of EA per mole of EC) to ester-interchange reaction in the presence of a catalyst preferably at the boiling point of the EA/ET azeotrope, driving off the EA/ET azeotrope formed with the progress of the reaction, and distilling the remaining reaction product to recover ECA. The Japanese Patent Publication states that the azeotrope which has been driven off and recovered is reacted with ethylene oxide as such to form EC, or the azeotrope is separated into EA and ET by extractive distillation with a suitable third component, and the separated ET is reacted with ethylene oxide to form EC. However, as stated hereinabove, it is impossible in practice to produce EC efficiently by reacting the azeotrope directly with ethylene oxide. Recovery of highly pure ET by the extraction and distillation of the azeotrope would be by no means easy. Aluminum alkoxides, isopropyl titanate, phosphoric acid and p-toluenesulfonic acid are exemplified as catalysts for use in the ester-interchange reaction. These catalysts homogeneously dissolve in the reaction mixture, and various difficulties are encountered in the separation or regeneration of these catalysts after the reaction. When an acid catalyst such as phosphoric acid and p-toluene-sulfonic acid is used, it must be neutralized before the purification of ECA. When an aqueous alkaline solution is added to the reaction mixture for neutralization, the same disadvantage as in the conventional esterification reaction is caused. Specifically, ET and EC which are completely soluble in water, and ECA and EA which have a fairly high solubility in water, are lost in the waste water. Moreover, the organic layer containing EA has a considerable amount of water dissolved therein to form $H_2O$/ET (b.p. 78.2° C.), $H_2O$/EA (b.p. 70.4° C.), $H_2O$/ET/EA (b.p. 70.2° C.), and EA/ET (b.p. 71.8° C.) azeotropes. Hence, the operation of recovering EA and ET is very much complicated.

When a metal alkoxide is used as a catalyst, problems also arise in post-treatment and in the activity of the catalyst. Specifically, the metal alkoxide catalyst is normally required to be removed as a hydroxide by hydrolysis with water or an acid prior to the distillation of the reaction mixture. Furthermore, its activity often varies from lot to lot, or depending upon the effect of moisture in the starting material. Thus, its handling and regeneration are also difficult.

The process for the continuous production of glycol ether acetate described in the U.S. Pat. (2) comprises the following steps:

(a) reacting an alkyl acetate with a glycol ether (1–3 moles of alkyl acetate per mole of glycol ether) in the presence of a catalyst selected from aluminum alkoxides, titanium alkoxides and dialkyl tin oxides, at a temperature of 150° to 225° C. and an elevated pressure of 25 to 150 psia;

(b) directing the equilibrium of the reaction to produce the desired glycol ether acetate by continuous distillative removal of the by-product alcohol from the reaction zone;

(c) withdrawing from the reaction zone a stream comprising catalyst and glycol ether acetate;

(d) separating the glycol ether acetate from the catalyst by flash distillation below 225° C.; and (e) purifying the glycol ether acetate by distillation.

The main conditions in this process are to use the starting alkyl acetate in an amount equivalent to, or usually in excess of, the glycol ether, to use a homogeneous catalyst of the type described above, to perform the reaction at specified high temperatures and pressures, and to remove the by-product alcohol continuously and distillatively from the reaction zone together with the formed alkyl acetate/alcohol azeotrope. The use of homogeneous catalysts brings about the same disadvantage as described above with regard to the method (1). The U.S. Patent states that the reaction temperature and pressure are selected to minimize the feed acetate component of the overhead stream removed from the reactor. However, such high temperatures and pressures are likely to cause decomposition of the product, and are economically disadvantageous. Since this process comprises fairly complex process steps, various difficulties would be experienced in its commercial performance.

It is an object of this invention to provide a process for continuously producing ethylene glycol monoethyl ether acetate from ethyl acetate and ethylene glycol monoethyl ether easily and economically without encountering the aforesaid various disadvantages of the prior art.

The process of this invention is especially characterized by the fact that ethylene glycol monoethyl ether in an amount exceeding that of ethyl acetate is reacted with the latter under mild conditions, that a strongly acidic cation exchange resin is used as a catalyst, and that a special distillation system coordinated with these conditions is used.

Thus, the present invention provides a process for continuously producing ethylene glycol monoethyl ether acetate by an ester-interchange reaction between ethylene glycol monoethyl ether and ethyl acetate, which comprises subjecting ethyl acetate and a stoichiometrically excess amount of ethylene glycol monoethyl ether to esterinterchange reaction in a reaction zone in the liquid phase in the presence of a strongly acidic cation exchange resin as a catalyst at a temperature not exceeding 100° C., said ethyl acetate and ethylene glycol monoethyl ether being continuously fed into the reaction zone; continuously sending the liquid reaction mixture from the reaction zone to a distillation column and distilling it to separate it into (a) an overhead fraction which is an azeotrope of the unreacted ethyl acetate and a part of by-product ethanol, (b) a liquid side stream fraction from an upper stage of the column which contains the remaining ethanol in a high concentration, (c) another liquid side stream fraction from another upper stage of the column which contains the unreacted ethylene glycol monoethyl ether in a high concentration, and (d) a bottom fraction comprising the resulting ethylene glycol monoethyl ether acetate;

recycling the fractions (a) and (c) to the reaction zone together with a fresh supply of ethyl acetate and ethylene glycol monoethyl ether; recovering the fraction (d) as a product; and sending the fraction (b) to another distillation system and distilling it to recover the by-product ethanol.

Preferred embodiments and advantages of the process of this invention are described below with reference to the accompanying drawing.

The drawing is a flow diagram for illustrating a preferred embodiment of the process of this invention in which (A) represents a material feed tank; (B), an esterinterchange reactor; (C), a first distillation column; (D), a second distillation column; (E), a third distillation column; and solid lines and dotted lines show flow paths for substances.

In tank (A), the EA/ET azeotrope (5) and EC (10) recycled from the distillation system are mixed with a fresh supply of EA (1) and EC (2). The resulting starting mixture (3) is continuously fed into reactor (B) where it is subjected to an ester-interchange reaction between EA and EC in the presence of a strongly acidic cation exchange resin catalyst.

In the starting mixture, EC must be present in a stoichiometrically excess amount relative to EA. The suitable amount of EC is 1.1 to 10 moles, preferably 2 to 5 moles, per mole of EA.

It has been found that ET in the recycled EA/ET azeotrope exerts no adverse effect on the ester-interchange reaction in the presence of a strongly acidic cation exchange resin catalyst.

Strongly acidic cation exchange resins used as a catalyst are well known and generally marketed. They are usually produced by introducing sulfonic groups into a styrene/divinylbenzene copolymer. Those cation exchange resins which are known as a porous type or macroreticular type are especially preferable because a high rate of reaction can be obtained with them. The catalyst can be used in the form of a fixed or fluidized bed. The fixed bed of catalyst is preferred from the standpoint of preventing the wear of resin particles. The stream of the reactant mixture may be directed downward or upward with respect to the fixed catalyst bed.

It has been found that the strongly acidic cation exchange resin catalyst used in the invention exhibits good activity under the reaction conditions of this invention, and this activity can be maintained over long periods of time. This catalyst has the further advantage that it can be separated from the reaction mixture without any difficulty because it is a solid catalyst insoluble in the reaction mixture as contrasted with the aforesaid homogeneous catalysts soluble in the reaction mixture used in the prior art.

The ester-interchange reaction in reactor (B) is carried out in the liquid phase at a relatively low temperature not exceeding 100° C., for example 20° to 100° C. Usually, temperatures of 20° to 90° C., preferably 30° to 80° C., are selected. At temperatures above 100° C., the catalyst tends to be degraded, and the amounts of by-product ethyl ether and high-boiling impurities increase. The reaction pressure is not critical so long as it is sufficient to maintain the reaction mixture in the liquid phase. Usually it is normal atmospheric pressure (1 kg/cm$^2$), but if desired, pressures of up to about 5 kg/cm$^2$.absolute can be used. The contact time is generally 0.2 to 5 hours, preferably 1 to 3 hours. An ECA selectivity of as high as 98% or more can be obtained under the aforementioned ester-interchange reaction conditions. Since this reaction is an equilibrium reaction as shown by equation (I), a higher conversion of EA is generally obtained when the mole ratio of EC to EA is higher. The unchanged reactants can be utilized without any substantial loss because they can be recycled to the reaction zone from the distillation system.

The catalyst-free reaction mixture (4) from reactor (B) is continuously fed into distillation column (C) where it is separated into the following four fractions (a) An overhead fraction (5) which is an azeotrope consisting of the unreacted EA and a part of by-product ET.

(b) A liquid side stream fraction (6) containing the remaining ET in a high concentration.

(c) Another liquid side stream fraction (10) containing the unreacted EC in a high concentration.

(d) A bottom fraction (12) consisting almost entirely of the resulting ECA.

The azeotrope overhead (5) is recycled to reactor (B) through tank (A). Since ET contained in the azeotrope does not adversely affect the reaction under the reaction conditions employed in this invention, it is possible to recycle the azeotrope directly and to re-use EA contained in it for the reaction. In other words, it is not necessary to separate EA from the azeotrope by a special means. Nor is it necessary to re-distill the azeotrope at a different pressure and to increase the EA concentration in the distillate. This is one reason why the amount of heat required for the process of this invention can be decreased.

One important characteristic feature of the distilling process in this invention is that side stream fractions (10) and (6) are taken out in liquid form from the upper stages of distillation column (C). When the ester-interchange reaction mixture obtained by using an excess of EC is distilled, a liquid zone containing the unreacted EC in a high concentration is formed in an upper stage of the distillation column, and side stream fraction (10) can be withdrawn from this liquid zone. On the other hand, a liquid zone containing the remaining ET (the excess of ET, which does not form the overhead azeotrope) in a high concentration is formed in another upper stage which is nearer to the top of the column, and side stream fraction (6) can be withdrawn from this liquid zone. This separation of side streams is possible by distillation of the reaction mixture obtained by ester-interchange reaction under EC-excess conditions, and is impossible in a reaction under EA-excess conditions as in the prior art.

The EC-rich fraction (10) withdrawn as a side stream is recycled to reactor (B) through tank (A) for reuse. The side stream fraction (6) containing the remaining ET in a high concentration, as will be described hereinbelow, is sent to the subsequent distillation system from which high purity ET can be easily recovered.

Separation of the side stream, especially the side stream fraction (10), in the present invention is one reason why the amount of heat required for the process of this invention can be small. In contrast, if an ordinary distillation system of evaporation-condensation is used to recover high boiling EC present in a relatively large amount for re-use, a large amount of heat would be required accordingly.

The bottom fraction (12) contains most of the resulting ECA and is recovered as the desired product. The bottom fraction sometimes contains a small amount of EC and traces of by-product high-boiling components. In this case, purified ECA can be simply obtained by using another distillation column.

Another characteristic of the distilling process of this invention is that the ECA product is directly withdrawn from the bottoms of the first distillation column (C). This means that in the distilling system in accordance with this invention, the frequency of exposure of ECA to high temperatures is reduced, and therefore, there is no likelihood of its loss by decomposition or of the secondary inclusion of impurities. If, on the other hand, the ester-interchange reaction mixture is subjected to an ordinary distillation system and the components are successively removed in the order of increasing boiling points, ECA having the highest boiling point is carried over to the final step of distillation, and therefore, the frequency of its exposure to high temperatures would increase.

The ET-rich side stream (6) contains a major amount of the remaining ET and small amounts of remaining EA and EC. If it is properly treated, it is easy to recycle EA and EC and recover remaining ET in pure form. The suitable treatment can be performed, for example, by using distillation columns (D) and (E) as shown in the accompanying drawing.

The side stream (6) is sent to distillation column (D), and from its top, a small amount of the EA/ET azeotrope (9) consisting of ET and all EA present is recovered. The azeotrope can be combined with the overhead azeotrope (5) of distillation column (C) and recycled to reactor (B). The bottom fraction (7) of column (D) which no longer contains EA but contains a major amount of ET and a small amount of remaining EC is sent to distillation column (E) from the top of which an ET fraction (8) is recovered and from the bottom of which an EC fraction (11) is recovered. The EC fraction (11) can be combined with the side stream (10) of column (C) and recycled to reactor (B). The overhead fraction (8) consists of high purity ET because the bottom fraction (7) of the column (D) no longer contains EA which has a boiling point close to ET and azeotropes with ET. Such a highly pure ET has the advantage that it can be directly reacted with ethylene oxide without prior extractive distillation or other troublesome purifying means, and can be utilized in the production of EC which is a starting material in the ester-interchange reaction.

As stated in detail hereinabove, the process for producing ECA in accordance with this invention is continuously performed. The main characteristic features of the process of this invention are that the ester-interchange reaction between EC and EA is carried out under mild conditions by using EC in molar excess, that a strongly acidic cation exchange resin, a solid catalyst, is used, and that the recovery of the product, the recycling of the unreacted materials and the recovery of by-products are effected by a unique distillation system coordinated with these reaction conditions. The advantages obtained by such a process are that the ester-interchange reaction can be continued stably and efficiently over long periods of time without involving troublesome problems such as the separation or regeneration of homogeneous catalyst, that the recovery of the reaction product and the recovery and recycling of the unreacted materials and by-products can be performed effectively and easily, and that the amount of heat required, i.e. the amount of steam consumed, in the distillation system can be considerably reduced. Thus, the process of this invention is very superior as a commercial process for ECA production.

The following Examples illustrate the present invention more specifically.

EXAMPLE 1

ECA was continuously produced in accordance with the flow diagram shown in the accompanying drawing.

A fixed bed-type reactor (B) was provided in which 200 liters of a sufficiently dried porous strongly acidic cation exchange resin having a matrix composed of a styrene/divinylbenzene copolymer [DIAION PK 228 (H-form), a registered trademark; the degree of crosslinking 14; the surface area 0.15 to 0.20 m$^2$/g; porosity 10%] was packed as a catalyst in the state swollen with EC. A starting mixture obtained by combining 8.2 kg/hr of fresh EC and 8.0 kg/hr of fresh EA with 71.6 kg/hr of a mixture of EC, EA and ET (the mole ratio of EA:EC=1:4) recycled from the subsequent distillation system in a material feed tank (A) was fed into the bottom of the reactor (B) at 65° C. under atmospheric pressure and reacted. The reaction mixture withdrawn from the top of the reactor was found to contain 14% of ECA (weight basis; the same basis will apply to other percentages), 11% of ET, 65% of EC, 9% of EA and 1% of other substances. Thus, the conversion of EA was 50.0%, and the ECA selectivity based on EC was 99.3%.

The reaction mixture was introduced into an approximately intermediate stage of distillation column (C) (with 90 trays), and distilled under atmospheric pressure. An EA/ET azeotrope (temperature 72° C.) was withdrawn from the top of the distillation column at a rate of 11.0 kg/hr, and recycled to the material feed tank (A). A liquid (temperature 89° C.) mainly containing ET was withdrawn from a portion near the top of the column (from the 18th tray), introduced into an intermediate stage of distillation column (D) (90 trays), and distilled under atmospheric pressure. An EA/ET azeotrope (temperature 72° C.) was recovered from the top of the column (D) at a rate of 1.5 kg/hr, and similarly to the above, recycled to the material feed tank (A). The bottom fraction (temperature 97° C.) of column (D) was fed into an intermediate stage of distillation column (E) (70 trays) operated under atmospheric pressure. ET having a purity of 100% was recovered from the top of the distillation column (E) at a rate of 4.2 kg/hr. From the bottom of distillation column (E), EC was withdrawn at a rate of 3.6 kg/hr. This EC was combined with a liquid (temperature 134° C.) containing EC and small amounts of EA, ET and ECA which was withdrawn from another upper stage (from the 30th tray) of distillation column (C) at a rate of 51.3 kg/hr, and recycled to the material feed tank (A). From the bottom of the distillation column (C), a liquid (temperature 159° C.) containing ECA, a small amount of EC and traces of high-boiling by-products was withdrawn. This bottom liquid was purified to afford the ECA product at a rate of 11.9 kg/hr.

The total amount of steam required for heating distillation columns (C), (D), and (E) was 46.7 kg/hr (1,900 Kcal as the amount of heat consumed per kilogram of ECA). After continuous operation for three months, there was hardly any appreciable degradation of the catalyst.

EXAMPLE 2

EA and EC were continuously reacted using the same reactor as used in Example 1 and 200 liters of a sufficiently dried porous strongly acidic cation exchange resin having a styrene/divinylbenzene copolymer matrix [DIAION PK 216 (H form), registered trademark; the degree of crosslinking 8; the surface area 0.15 to 0.20 m$^2$/g; porosity 10%] as a catalyst. The reaction mixture was continuously separated into the individual components by a combination of reduced pressure distillation column (C) and atmospheric pressure distillation columns (D) and (E).

A starting mixture (EA:EC mole ratio=1:3) obtained by combining fresh EC (9.8 kg/hr) and EA (9.6 kg/hr) in material feed tank (A) with a mixture (68.3 kg/hr) of EC, EA and ET recycled from the subsequent distillation system was fed into the reactor at 65° C. under atmospheric pressure, and reacted. The reaction mixture withdrawn from the top of the reactor was found to contain 18% of ECA, 11% of ET, 12% of EA, 58% of EC and 1% of other substances. Thus, the conversion of EA was 48.0%, and the ECA selectivity based on EC was 98.8%.

The reaction mixture was introduced into an approximately intermediate stage of distillation column (C) (with 90 trays), and distilled under reduced pressure (210 mmHg ab.). An EA-ET azeotrope (temperature 40° C.) was withdrawn from the top of the column (C) at a rate of 13.4 kg/hr, and recycled to the material feed tank (A). A liquid (temperature 56° C.) containing remaining ET was withdrawn from a portion (from the 18th tray) near the top of the column, and introduced into that tray of distillation column (D) (with 30 trays) which was located at a position corresponding to about one-third of the total height of the column from its bottom, and distilled under atmospheric pressure. From the top of the column (D) an EA-ET azeotrope (temperature 72° C.) was recovered at a rate of 0.6 kg/hr, and recycled to the material feed tank (A) in the same manner as above. A bottom fraction (temperature 97° C.) from column (D) was fed into an intermediate stage of distillation column (E) (with 70 trays) operated under atmospheric pressure, and ET having a purity of 100% was recovered from its top at a rate of 5.0 kg/hr. From the bottom of the column (E), EC was withdrawn at a rate of 1.7 kg/hr. This EC was combined with 47.7 kg/hr of a liquid (temperature 102° C.) containing EC and small amounts of EA, ET and ECA which was withdrawn from an intermediate stage (from the 30th tray) of the distillation column (C), and recycled to the material feed tank (A). From the bottom of the distillation column (C), a liquid (temperature 124° C.) containing ECA, a small amount of EC, and traces of high-boiling by-products was withdrawn. This liquid was purified to obtain ECA product at a rate of 14.3 kg/hr.

The total amount of steam required for the heating of distillation columns (C), (D) and (E) was 47.4 kg/hr (1,660 Kcal as the amount of heat consumed per kilogram of ECA). After continuous operation for 3 months, there was hardly any appreciable degradation of the catalyst.

EXAMPLE 3

A continuous operation was performed using a small-sized apparatus.

A fixed bed-type tubular reactor equipped with a stainless steel jacket was used in which 100 ml of pre-dried EC-swollen porous strongly acidic cation exchange resin DIANION PK 216 was packed as a catalyst. A starting mixture (EA:EC mole ratio=1:3.9) was prepared in a mixer by mixing fresh EC (10.0 g/hr) and EA (9.8 g/hr) with an EA/ET azeotrope (11.1 g/hr; ET 31% by weight) and EC (60.9 g/hr) recovered from the subsequent separating steps. The starting mixture was fed upwardly at a rate of 100 ml/hr into the reactor maintained at 65° C. and atmospheric pressure. The reaction mixture discharged from the reactor was analyzed by gas chromatography in a conventional manner, and was found to contain 15.8% of ECA, 9.3% of ET, 8.3% of EA, 66.3% of Ec and 0.3% of other substances. Hence, the conversion of EA was 55.9%, and the ECA selectivity based on EC was 98.8%. After continuous operation for three months, there was hardly any appreciable degradation of the catalyst.

EXAMPLE 4

A continuous operation was performed under somewhat varied conditions using the same type of reactor as used in Example 3 and a porous strongly acidic cation exchange resin having a styrene/divinylbenzene copolymer matrix [Amberlyst 15, registered trademark; the degree of crosslinking 16; the surface area 4.3 m²/g; porosity 32%] as a catalyst.

Fresh EC (12.0 g/hr) and EA (11.6 g/hr) were mixed in a mixer with an EA-ET azeotrope (17.4 g/hr; ET 31% by weight) and EC (48.4 g/hr) recovered from the subsequent separating steps to provide a starting mixture having an EA:EC molar ratio of 1:2.5. The starting mixture was fed at a rate of 100 ml/hr upwardly into the reactor maintained at 70° C. and 2 kg/cm². The reaction mixture was found to contain 19.4% of ECA, 12.8% of ET, 13.4% of EA, 54.1% of EC and 0.3% of other substances. Hence, the conversion of EA was 49.3%, and the ECA selectivity based on EC was 98.2%.

COMPARATIVE EXAMPLE 1

In this Comparative Example, EC was used in excess of SA as in Examples 1 to 4. However, separation of the resulting reaction mixture into the individual components was performed by a different distillation system from that used in Examples 1 to 4. This distillation system was an ordinary distillation system adapted to distill the components successively in the order of increasing boiling points and thus to recover ECA having the highest boiling point in the final step of distillation. It was found that when such a distillation system was used, the amount of heat consumed for distillation was larger than that in the distillation system of the present invention.

The same reactor and catalyst as described in Example 1 were used. A starting mixture (EA:EC mole ratio=1:3) obtained by combining fresh EC (9.4 kg/hr) and EA (9.2 kg/hr) in the material supply tank (A) with a mixture of EA, EC and ET (68.0 kg/hr) recycled from the subsequent distillation system was fed into the bottom of the fixed bed-type reactor (B) at 65° C. and atmospheric pressure, and reacted. The reaction mixture withdrawn from the top of the reactor contained 16% of ECA, 10% of ET, 60% of EC, 13% of EA and 1% of other substances. Thus, the conversion of EA was 45.2%, and the ECA selectivity based on EC was 99.0%.

This reaction mixture was introduced into that tray of a first distillation column (with 70 trays) which was located at a position corresponding to about one-third of the total height of the column from its bottom, and distilled under reduced pressure (210 mmHg ab.). An EA/ET azeotrope (temperature 40° C.) was withdrawn from the top of the column at a rate of 15.7 kg/hr, and recycled to the material feed tank (A). The bottom fraction (temperature 97° C.) was fed into that tray of a second distillation column (with 50 trays) which was located at a position corresponding to about one-third of the total height of the column from its bottom, and distilled under atmospheric pressure. From the top of the second column, ET having a fairly high purity was distilled out at a rate of 4.8 kg/hr and recovered. In the meantime, the bottom fraction (temperature 149° C.) from the second distillation column was introduced into that tray of a third distillation column (with 70 trays) which was located at a position corresponding to about one-third of the total height of the column from its bottom, and distilled at atmospheric pressure. A distillate (temperature 135° C.) containing EC as a main component was withdrawn from the top of the third column at a rate of 53.3 kg/hr, and recycled to the material feed tank (A). From the bottom of the third distillation column, a liquid (temperature 168° C.) containing ECA and small amounts of EC and high-boiling by-products was withdrawn. It was purified to afford 13.7 kg/hr of ECA product.

In operating the distillation columns, the overhead steam of the third distillation column was used to heat the first distillation column. The total amount of steam required to heat the three distillation columns was 61.6 kg/hr (2,250 Kcal as the amount of heat consumed per kilogram of ECA).

It will be appreciated that the amounts of heat consumed in Examples 1 and 2 were substantially smaller than that consumed in this Comparative Example.

COMPARATIVE EXAMPLE 2

This example shows a reaction which was performed by using EA in excess of EC. The reaction mixture obtained by this reaction cannot be treated by the distillation system used in the present invention. Accordingly, it was treated by using the following three distillation columns. In this example, the amount of steam required to heat the distillation system was larger than that required in Comparative Example 1.

The reactor and catalyst used were the same as those used in Example 1, and 70 liters of the catalyst was packed in the reactor.

In material feed tank (A), fresh EC (8.2 kg/hr) and EA (8.0 kg/hr) were combined with 47.5 kg/hr of a liquid containing EA and EC which was recycled from a third distillation column. The resulting mixture (EA:EC mole ratio=3:1) was fed into reactor (B) at 60° C. and atmospheric pressure, and reacted. The reaction mixture withdrawn from the top of the reactor was found to contain 19% of ECA, 7% of ET, 59% of EA, 12% of EC and 3% of other substances. Hence, the conversion of EC was 52%, and the ECA selectivity based on EC was 99.4%.

The reaction mixture was introduced into an intermediate stage of a first distillation column (with 160 trays) operated at 4260 mmHg ab.. An EA/ET azeotrope (temperature 126° C.) distilled out from the top of the column at a rate of 11.6 kg/hr was subsequently introduced into an intermediate stage of a second distillation column (with 140 trays). An EA/ET azeotrope (temperature 72° C.) was withdrawn from the top of the second distillation column at a rate of 7.4 kg/hr. This azeotrope was recycled to the feed section of the first distillation column. From the bottom of the second distillation column, excessive ET (4.2 kg/hr; temperature 86° C.) formed due to a difference in the composition of azeotrope caused by a difference in pressure was separated. In the meantime, 59.5 kg/hr of the liquid (temperature 154° C.) withdrawn from the bottom of the first distillation column was fed into the third distillation column (with 120 trays), and distilled under atmospheric pressure. A mixture (temperature 82° C.) containing 37.9 kg/hr of EA and 7.5 kg/hr of EC was distilled out from the top of the third column, and recycled to the material feed tank (A).

Thus, a liquid (temperature 163° C.) containing ECA and small amounts of EC and high-boiling by-products was withdrawn from the bottom of the third distillation column, and purified to form ECA product at a rate of 11.8 kg/hr.

The total amount of steam required for heating the three distillation columns was 55.2 kg/hr (2,320 Kcal as the amount of heat consumed per kilogram of ECA).

Separately, a small-scale test was performed in this reaction system for the deterioration of the activity of the catalyst. It was found that after three months continuous operation, the catalyst was deteriorated.

What we claim is:

1. A process for continuously producing ethylene glycol monoethyl ether acetate by an ester-interchange reaction between ethylene glycol monoethyl ether and ethyl acetate, which comprises
   (1) subjecting ethyl acetate and a stoichiometrically excess amount of ethylene glycol monoethyl ether to the ester-interchange reaction in a reaction zone in the liquid phase in the presence of a strongly acidic cation exchange resin as a catalyst at a temperature not exceeding 100° C., said ethyl acetate and ethylene glycol monoethyl ether being continuously fed into the reaction zone;
   (2) continuously sending the liquid reaction mixture from the reaction zone to a distillation column and distilling the mixture to separate it into
      (a) an overhead fraction which is an azeotrope of unreacted ethyl acetate and a part of by-product ethanol,
      (b) a liquid side stream fraction from an upper stage of the column whose major component is a majority of the remaining by-product ethanol,
      (c) another liquid side stream fraction from another upper stage of the column whose major component is unreacted ethylene glycol monoethyl ether, and
      (d) a bottom fraction comprising the resulting ethylene glycol monoethyl ether acetate;
   (3) recycling the fractions (a) and (c) to the reaction zone together with a fresh supply of ethyl acetate and ethylene glycol monoethyl ether;
   (4) recovering the fraction (d) as a product; and
   (5) sending the fraction (b) to another distillation system and distilling it to recover by-product ethanol.

2. The process of claim 1 wherein the mole ratio of ethyl acetate to ethylene glycol monoethyl ether to be reacted is from 1:1.1 to 1:10.

3. The process of claim 2 wherein the mole ratio of ethyl acetate to ethylene glycol monoethyl ether is from 1:2 to 1:5.

4. The process of claim 1 wherein the catalyst is a porous or macroreticular strongly acidic cation exchange resin.

5. The process of claim 1 wherein the reaction temperature is 20° to 100° C.

6. The process of claim 5 wherein the reaction temperature is 20° to 90° C.

7. The process of claim 5 wherein the reaction temperature is 30° to 80° C.

8. The process of claim 1 wherein the pressure of the reaction zone is 1 to 5 kg/cm$^2$.absolute.

9. The process of claim 8 wherein the pressure of the reaction zone is 1 kg/cm$^2$.absolute.

* * * * *